(12) United States Patent
Higgins et al.

(10) Patent No.: US 9,151,738 B2
(45) Date of Patent: Oct. 6, 2015

(54) SOLVENT EXTRACTION USING ENVIRONMENTALLY-FRIENDLY SILOXANE SOLVENTS

(71) Applicant: Agilent Technologies, Inc., Loveland, CO (US)

(72) Inventors: Franklin Scott Higgins, Naugatuck, CT (US); John Arthur Seelenbinder, Watertown, CT (US)

(73) Assignee: Agilent Technologies, Inc., Santa Clara, CA (US)

(*) Notice: Subject to any disclaimer, the term of this patent is extended or adjusted under 35 U.S.C. 154(b) by 33 days.

(21) Appl. No.: 13/898,867

(22) Filed: May 21, 2013

(65) Prior Publication Data

US 2014/0349406 A1  Nov. 27, 2014

(51) Int. Cl.
*G01N 33/18* (2006.01)

(52) U.S. Cl.
CPC ........... *G01N 33/1833* (2013.01); *Y10T 436/21* (2015.01); *Y10T 436/24* (2015.01); *Y10T 436/255* (2015.01)

(58) Field of Classification Search
CPC .............. G01N 33/18; G01N 33/1826; G01N 33/1833; Y10T 436/21; Y10T 436/24; Y10T 436/25; Y10T 436/255
USPC ............. 436/60, 72, 139, 171, 173, 174, 177, 436/178; 422/82.09, 527
See application file for complete search history.

(56) References Cited

U.S. PATENT DOCUMENTS

| | | | |
|---|---|---|---|
| 5,037,557 A | | 8/1991 | Warrenchak et al. |
| 2009/0004748 A1* | | 1/2009 | Ganesan .................... 436/28 |
| 2014/0018600 A1 | | 1/2014 | Pronovost et al. |

FOREIGN PATENT DOCUMENTS

| | | |
|---|---|---|
| DE | 3539525 | 5/1987 |
| SU | 975041 | 11/1982 |

OTHER PUBLICATIONS

Barnett et al. BMC Dermatology, vol. 12:15, Sep. 3, 2012, pp. 1-5.*
ASTM International, Designation: D7678-11, Standard Test Method for Total Petroleum Hydrocarbons (TPH) in Water Wastewater with Solvent Extraction using Mid-IR Laser Spectroscopy. (2011).
EPA Storet No. 00560, Method 413.2 (Spectrophotometric, Infrared), Oil and Grease, Total Recoverable. (1974).
EPA Storet No. 45501, Method 418.1 (Spectrophotometric, Infrared), Petroleum Hydrocarbons, Total Recoverable. (1978).
EPA Method 1664, Revision A: N-Hexane Extractable Material (HEM; Oil and Grease) and Silica Gel Treated N-Hexane Extractable Material (SGT-HEM; Non-polar Material) by Extraction and Gravimetry, United States Environmental Protection Agency Office of Water, Washington, DC 20460, EPA-821-R-98-002 PB99-121949, Feb. 1999.
ASTM International, Designation: D 3921-96 (Reapproved 2003), Standard Test Method for Oil and Grease and Petroleum Hydrocarbons in Water. (1996).
ASTM International, Designation: D 7066-04, Standard Test Method for dimer/trimer of chlorotrifluoroethylene (S-316) Recoverable Oil and Grease and Nonpolar Material by Infrared Determination (2004).
Alimzhanova, et al. "CAPLUS, disclosing polydimethylsiloxane fiber coating extraction to quantify total petroleum hydrocarbons", Eurasian Chemico-Technological Journal, 14(2), 177-182, 2012.
Combined Search and Examination Report mailed Oct. 6, 2014 in GB Application No. 1406307.7.
Office Action mailed Jul. 20, 2015 in UK Application No. GB1406307.7.

* cited by examiner

*Primary Examiner* — Maureen Wallenhorst

(57) ABSTRACT

Solvent extraction to quantify contamination of a sample by a hydrocarbon contaminant is performed by providing a defined quantity of the sample, providing a defined quantity of a siloxane solvent, mixing the defined quantity of the siloxane solvent and the defined quantity of the sample to extract the hydrocarbon contaminant from the sample to form a contaminant solution with the siloxane solvent, and separating the contaminant solution from the sample. A concentration of the hydrocarbon contaminant in the contaminant solution can be measured by vibrational spectroscopy. Siloxane solvents are CFC free, VOC exempt, odorless, colorless, low to moderately flammable, non-toxic, and safe for incidental skin contact. Some are even used in cosmetic products.

22 Claims, 8 Drawing Sheets

MicroLab

User: admin
Result: D4 Prep 10, u732 dp6 r1_2012-06-20T17-02-14

180

| Solvent Type | Date Sample Taken | |
|---|---|---|
| Hours Since Last Analysis | Date Sample Analyzed | |
| Date of Manufacture | Location | |

Results:

| Name | Value | Low Threshold | High Threshold |
|---|---|---|---|
| Total Petroleum Hydrocarbons (TPH, mg/L) | 9.71 | | |

[Home] [Data Handling] [Details] [Params] [Results]

*Fig. 3*

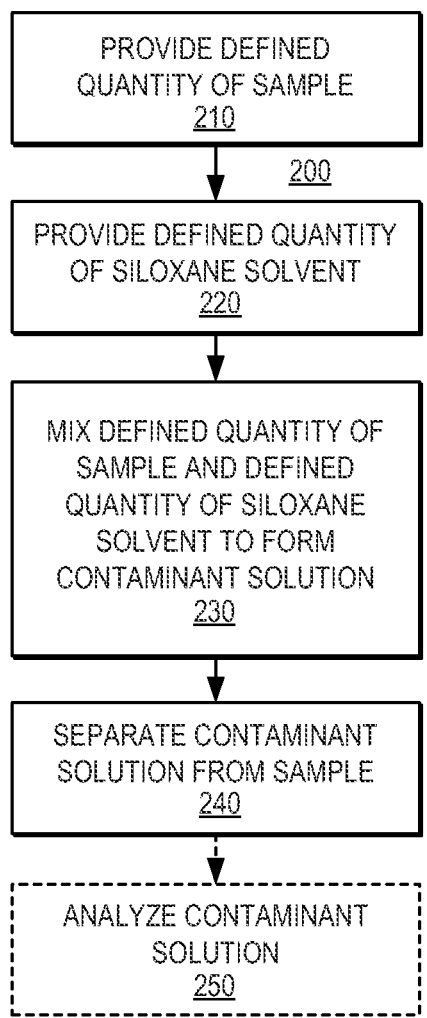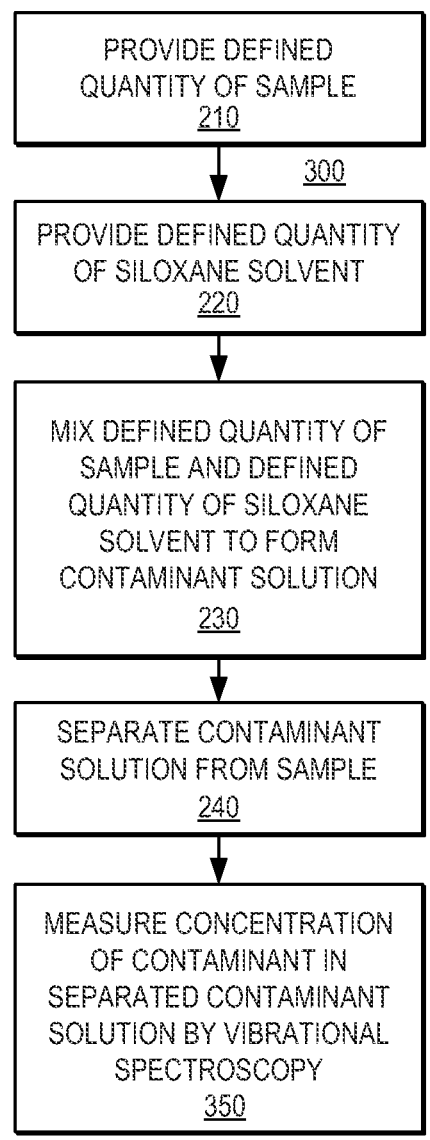
Fig. 4
Fig. 5

SOLVENT EXTRACTION USING ENVIRONMENTALLY-FRIENDLY SILOXANE SOLVENTS

BACKGROUND

A common environmental measurement measures the concentration of a hydrocarbon contaminant, such as oil, in a sample, such as a sample of water, or a sample of a particulate matrix, such as soil. Several ASTM methods have been released for measuring the concentration of oil in water, including D7678-11, D3921, and D7066-04. These methods involve adding a defined quantity of a solvent to a defined quantity of a sample of water and agitating the resulting mixture. The solvent has low solubility in water and is a good solubilizer of the contaminant. The mixture is left to separate, and a defined quantity of a solution composed of the contaminant extracted from the water dissolved in the solvent is drawn off and put in the measurement cell of an infrared spectrometer. The spectrometer measures the absorption of infrared light by the solution at a defined infrared wavelength or in a defined infrared wavelength range. Software associated with the spectrometer converts the absorption measurement to a measurement of the concentration of the hydrocarbon contaminant in the sample. Alternatively, a method exists for liquid-liquid extraction followed by gravimetric determination, EPA 1664. Each of these methods can be used to measure of total oil and grease (TOG) and, after filtration, total petroleum hydrocarbons (TPH) and total grease (TG). TPH is highly regulated with respect to water discharge.

Solvent extraction methods originally used such solvents as carbon tetrachloride and carbon disulfide as the solvent. However, these solvents are harmful to the central nervous system and are harmful in other ways, so that their use was discontinued. Present-day solvent extraction methods use solvents that are either halogenated or contain volatile organic hydrocarbons (VOC). Halogenated solvents are expensive to purchase and to dispose of. Moreover, halogenated compounds are typically ozone depleting and are often toxic to marine life if they are released in waste water. Petroleum-based solvents are considered by many governments to contribute to global warming.

The newest technique specified in ASTM D7678-11 uses cyclohexane as the solvent. Cyclohexane has the disadvantage that it is also a hydrocarbon. ASTM D7678-11 measures the infrared absorbance of methyl groups ($CH_3$) in hydrocarbons, since cyclohexane has no methyl group absorbance. The problem is that infrared absorption by the methyl group used in the cyclohexane methods is typically four times weaker than infrared absorption by the methylene groups ($CH_2$) that can be used with other solvents. The weaker absorption results in more variability in the results at low contaminant levels. Furthermore, the solvents used in ASTM D7678-11 (cyclohexane) and EPA 1664 (hexane) are both highly flammable, unhealthy to breathe (personnel exposure limits must be complied with), their vapors may have greenhouse gas contributions, and are subject to U.S. Federal VOC regulations.

Accordingly, what is needed for use in solvent extraction methods is a solvent that is non-toxic, has low to moderate flammability, is inexpensive to purchase and to dispose of, and that does not harm the environment.

BRIEF DESCRIPTION OF THE DRAWINGS

FIG. 3 is a screenshot showing how the MicroLab PC software displays a result for TPH derived from each spectral measurement performed by a vibrational spectrometer.

FIG. 4 is a flowchart showing an example of a method for performing solvent extraction to quantify contamination of a sample by a hydrocarbon contaminant.

FIG. 5 is a flowchart showing an example of a method for determining the concentration of a hydrocarbon contaminant in a sample.

DETAILED DESCRIPTION

Figure 1:
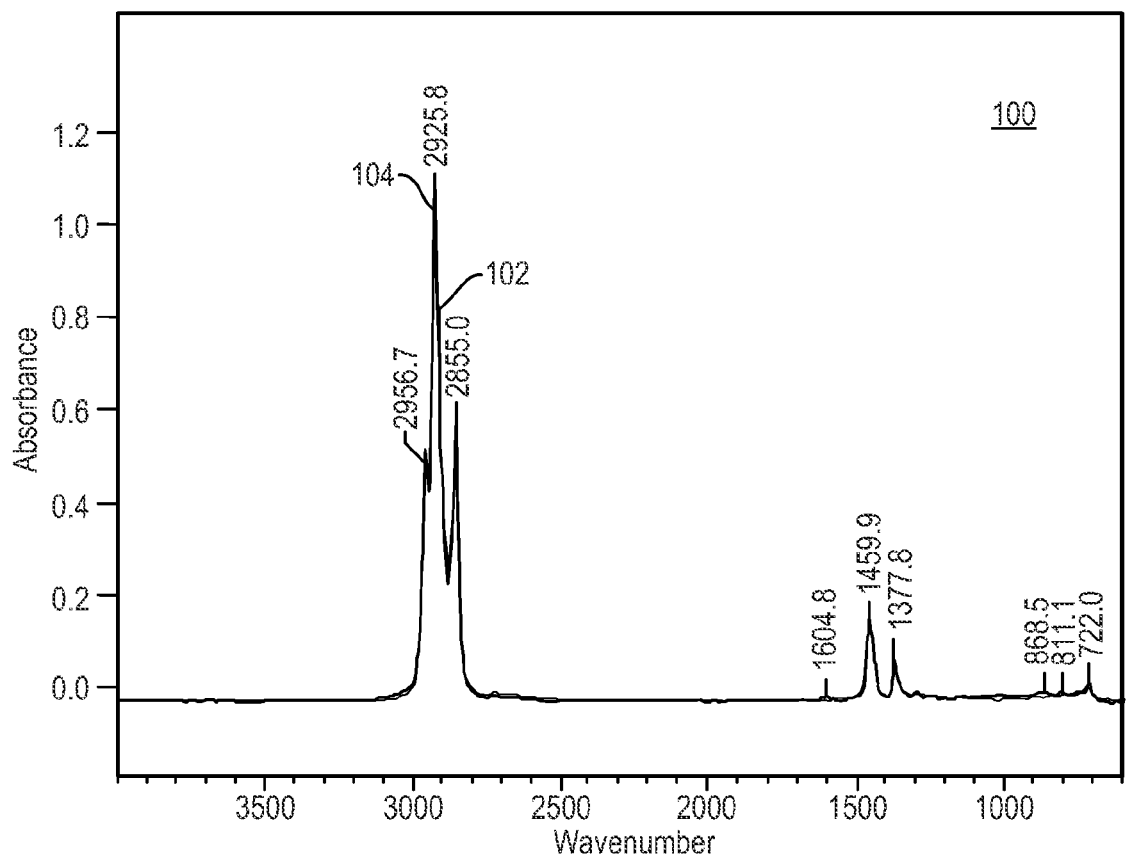
FIG. 1 is a graph showing the FTIR spectrum of a common mineral oil at and the FTIR spectrum of crude oil at overlaid on the mineral oil FTIR spectrum.

Disclosed herein is a method for performing solvent extraction to quantify contamination of a sample by a hydrocarbon contaminant. In the method, a defined quantity of the sample is provided, a defined quantity of a siloxane solvent is provided, the defined quantity of the sample and the defined quantity of the siloxane solvent are mixed to extract the hydrocarbon contaminant from the sample to form a contaminant solution with the siloxane solvent. The contaminant solution is then separated from the sample.

Also disclosed herein is a method for determining the concentration of a hydrocarbon contaminant in a sample. In the method, a defined quantity of the sample is provided, a defined quantity of a siloxane solvent is provided, the defined quantity of the sample and the defined quantity of the siloxane solvent are mixed to extract the hydrocarbon contaminant from the sample to form a contaminant solution with the siloxane solvent, the contaminant solution is separated from the sample, and the concentration of the contaminant in the separated contaminant solution is measured by vibrational spectroscopy.

A siloxane solvent is a clear, colorless, odorless and non-toxic liquid solvent that includes monomers or polymers each having at least one silicon atom bonded to a respective oxygen atom and to an organic moiety, such as a methyl group. Apart from a relatively weak methyl stretch absorbance at a wave number of $2966\ cm^{-1}$, siloxane solvents have an infrared absorption spectrum substantially devoid of absorption peaks that overlap the strong methyl and methylene absorption peaks of hydrocarbons, e.g., those in wave number ranges from $3200\ cm^{-1}$ to $2700\ cm^{-1}$ (particularly, from $2890\ cm^{-1}$ to $2790\ cm^{-1}$) and from $1800$ to $1300\ cm^{-1}$ (particularly at $1460\ cm^{-1}$ and at $1377\ cm^{-1}$)). Examples of siloxane solvents suitable for use in the methods described herein include the following:

TABLE 1

| Name | INCI Name | Commercial Name | Viscosity (cSt) |
|---|---|---|---|
| Hexamethyldisilaxane | Disiloxane | Xiameter ® PMX-200 0.65CS Silicone Fluid | 0.65 |
| decamethyltetrasiloxane | Dimethicone | Xiameter ® PMX-200 1.5CS Silicone Fluid | 1.5 |
| polydimethysiloxane 5 cst | Dimethicone | Xiameter ® PMX-200 5CS Silicone Fluid | 5.0 |
| polydimethyisiloxane 20 cst | Dimethicone | Xiameter ® PMX-200 20CS Silicone Fluid | 20 |
| polydimethylsiloxane 100 cst | Dimethicone | Xiameter ® PMX-200 100CS Silicone Fluid | 100 |
| polydimethylsiloxane 500 cst | Dimethicone | Xiameter ® PMX-200 500CS Silicone Fluid | 500 |
| phenylmethylsiloxane (dimethyl, phenylmethyl siloxane, trimethyl-terminated) | | Dow Corning 510 ® Fluid 50 cst | 50 |
| Cyclotetrasiloxane, e.g., octamethylcyclo-tetrasiloxane (cyclo-2244 D4 cyclomethicone) (polydimethylcyclosiloxane) | | | 2.5 |

Alternative names for some of the siloxane solvents are set forth in parentheses in Table 1.

Siloxane solvents are not harmful to the ozone layer and are not considered to contribute to global warming. Siloxane solvents have low toxicity to marine aquatic life. Disposal of siloxane solvents is easy and inexpensive: they can be absorbed onto clay or vermiculite that is then disposed of as solid waste. The chemical composition of siloxane solvents allows them to be used for measuring the concentrations of hydrocarbons in samples of water or particulate matrices such as soil using many different vibrational and non-vibrational measurement techniques.

Siloxane solvents are much less expensive to purchase, store, and dispose of than the halogenated solvents or petroleum-based cyclohexane and hexane solvents used in other liquid-liquid extraction methods. Some of the siloxane solvents suitable for use in the above methods are also used in cosmetics as a volatile carrier and are therefore very safe to handle. Siloxane solvents are exempt from US federal VOC regulations (including CARB and OTC).

Siloxane solvents have properties that make them highly suitable for performing solvent extraction suitable for measuring the concentration of hydrocarbon contaminants in samples of water: they have low solubility in water, but are good solubilizers of hydrocarbon oils, petroleum-based oils, and grease (triglyceride ester oils). Grease is defined as any plant or animal triglyceride based oil (e.g., a vegetable oil) and is not considered a marine pollutant. Grease absorbs infrared light in a so-called ester region (1750 $cm^{-1}$ to 1720 $cm^{-1}$). Siloxane solvents also have properties that make them highly suitable for performing solvent extraction suitable for measuring the concentration of hydrocarbon contaminants in particulate matrices such as sand or soil: such particulate matrices have low solubility in siloxane solvents, but siloxane solvents are good solubilizers of the hydrocarbon oils, petroleum-based oils, and grease (triglyceride ester oils) that can contaminate such particulate matrices.

Siloxane solvents have infra-red (IR) spectra that allow the stronger hydrocarbon IR bands to be used for measuring the concentration of hydrocarbon contaminants in contaminant solutions obtained by mixing a siloxane solvent with a sample containing the contaminant, e.g., a contaminant solution of oil extracted from water or from a particulate matrix. The IR spectra of siloxane solvents additionally have an ester region that can be used to measure the concentration of grease dissolved therein.

The above attributes make siloxane solvents safer, greener, and less expensive alternatives to the solvents that are currently used to extract hydrocarbon contaminants from water or particulate matrices for measurement by vibrational spectroscopic and other techniques. In an example, cyclo-2244 D4 cyclomethicone (octamethylcyclotetrasiloxane) ([—Si$(CH_3)_2$O—]$_4$), referred to herein as D4 cyclomethicone, for brevity, is used as the siloxane solvent. D4 cyclomethicone is in a class of compounds called organosilanes, which are also known as silicone oils. Many other members of this class share the desirable properties of D4 cyclomethicone and are suitable for use as a siloxane solvent.

Measurement methods based on vibrational spectroscopy are faster and simpler to operate than gas chromatography-based methods such as ISO 9377-2. However, hitherto, the hazardous chemicals used in sample preparation for current vibrational spectroscopy-based measurement methods limit the application of these methods. This is especially true for field-based measurements. The methods disclosed herein allow measurement to be performed on-site due to their use of a safe and easy-to-handle siloxane solvent. Performing measurements on-site provides a cost advantage due to a reduction in shipping costs. Additionally, performing measurements on-site potentially provides more accurate results since it reduces the risk of deterioration of the sample during shipping, and/or as a result of exposure to extremes of temperature. In some cases, excessive time in transit allows hydrocarbons in the sample to oxidize, which changes the result of the assay. Performing measurements on-site additionally allows measurements that produce anomalous results to be promptly repeated.

All the organic components of petroleum-based or natural oils, such as grease, are measurable by vibrational spectroscopy such as infrared spectroscopy or Fourier transform infrared (FTIR) spectroscopy. Modern portable IR spectrometers can scan the entire mid-IR spectrum to provide detailed chemical composition information about the sample. Portable spectrometers with sample preparation using a safe and easy-to-handle siloxane solvent make possible on-site measurements of total petroleum hydrocarbons (TPH), total grease (TG), and total oil and grease (TOG).

The methods disclosed herein can be used to measure, or to prepare samples for measuring, the concentration of oil in water and oil in particulate matrices in such locations as oil depots, refineries, offshore rigs, and environmental conservation locations. The methods can be used in such applications as monitoring the efficiency of oil/water separation systems, and surveying water and soil quality at superfund or hazardous waste sites.

The methods disclosed herein are based on ASTM oil-in-water measurement methodologies, ASTM D3921-96 and ASTM D7678-11. However, the methods disclosed herein use a CFC-free, VOC-exempt, odorless, colorless, and non-toxic-to-skin siloxane solvent. The siloxane solvent replaces conventional halogenated solvents, such as the chlorofluorocarbon solvent and the fluorinated trimer (S-316) solvent used in ASTM D3921 and ASTM D7066-04 respectively. Chlorofluorocarbons and other halogenated solvents have been banned by the Montreal protocol due to their ozone-depleting activity. The measurement methods disclosed herein perform vibrational spectroscopy in a similar IR absorbance region as ASTM D3921-96 and use the same sample preparation and calibration techniques as ASTM D7678-11. However, the highly flammable cyclohexane solvent used in ASTM D7678-11 is replaced with a siloxane solvent having low to moderate flammability, such as D4 cyclomethicone. Some changes are made in the spectroscopic parameters to accommodate the unique IR signature of the siloxane solvent. Apart from the use of a different solvent, the standard procedures for solvent extraction of hydrocarbon contaminants from water remain unchanged from previous ASTM methods. The ASTM-based calibrations and results described here will correlate to ASTM D3921, ASTM D7066, ASTM D7678-11, ISO 9377-2, EPA 1664, EPA 413.2, and 418.1 methods.

The methods disclosed herein have a limit of quantitation (LOQ) of 0.75 mg/L (0.75 ppm) for oil in water with an upper limit at 400 mg/L (400 ppm) without dilution or an upper limit of 1200 mg/L (1200 ppm) with a 3× dilution.

Crude oil is a mixture of hydrocarbons (HCs) with different chemical compositions, but most of crude oil exists as long-chain HCs (mineral oil and paraffinic), aromatics, and lighter short-chain hydrocarbons. FIG. 1 is a graph 100 showing the FTIR spectrum of a common mineral oil at 102 and the FTIR spectrum of crude oil at 104 overlaid on the mineral oil FTIR spectrum 102. The aromatics and short-chain hydrocarbons are commonly referred to as lights and are more miscible with water than long-chain hydrocarbons. Long-chain hydrocarbons are particularly harmful to the environment due to their persistence in water and their tendency to form layers on top of water that contaminate shoreline aquatic ecosystems.

Methylene (R—$CH_2$—R) and methyl (R—$CH_3$) functional groups are present in both long- and short-chain aliphatic hydrocarbons, as well as in most of the lighter aromatic hydrocarbons (such as toluene, xylenes, and ethyl benzene) in crude oil. When a siloxane solvent is used to extract a hydrocarbon contaminant from a sample to form a contaminant solution, the concentration of aliphatic methylene and methyl symmetric CH stretching groups present in the contaminant solution can be measured using infrared, e.g., FTIR, spectroscopy in a wave number range extending from 2890 $cm^{-1}$ to 2790 $cm^{-1}$ (corresponding to a wavelength range of 3.46-3.59 micrometers (μm)).

Figure 2:
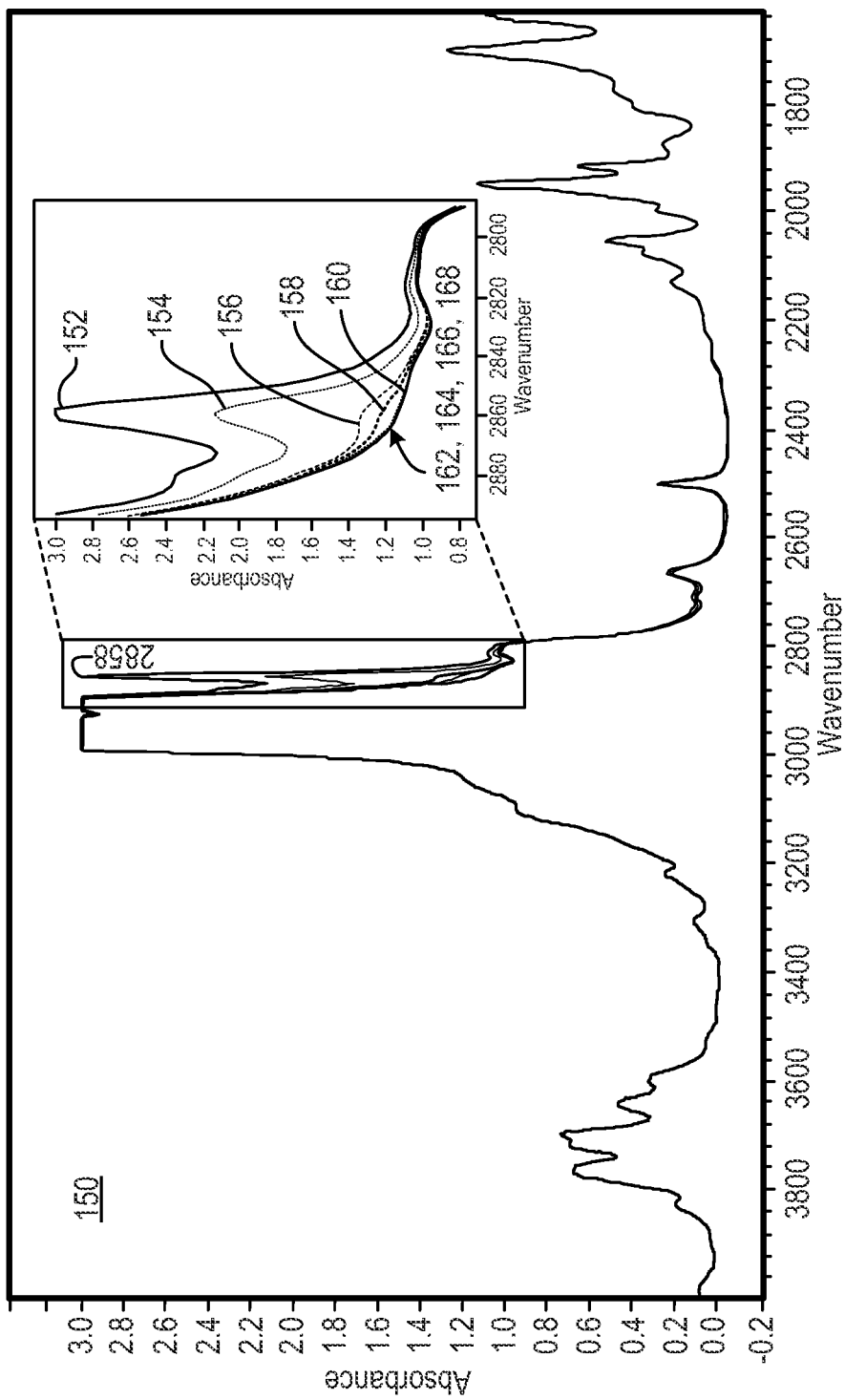
FIG. 2 is a graph showing overlaid FTIR spectra of contaminant solutions with different concentrations of an exemplary hydrocarbon contaminant (tetradecane) in an exemplary siloxane solvent (D4 cyclomethicone).
Figure 7:
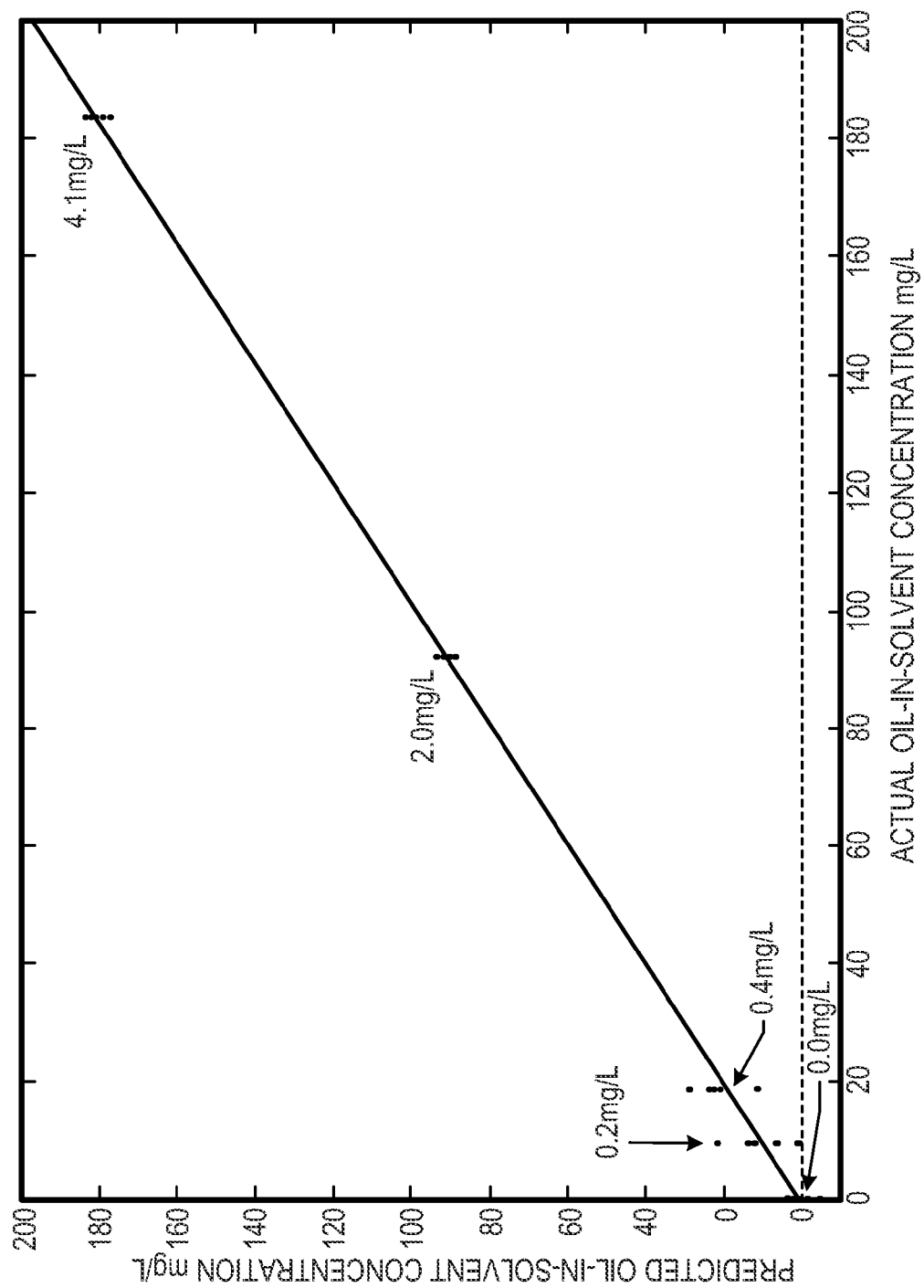
FIG. 7 is a predicted-versus-actual graph showing the results of the low-range calibration performed as described above using calibration samples of tetradecane in D4 cyclomethicone.

FIG. 2 is a graph 150 showing overlaid FTIR spectra of contaminant solutions with different concentrations of an exemplary hydrocarbon contaminant (tetradecane) in an exemplary siloxane solvent (D4 cyclomethicone). Specifically, the spectrum of a contaminant solution with a contaminant concentration of 400 mg/L is shown at 152, the spectrum of a contaminant solution with a contaminant concentration of 200 mg/L is shown at 154, the spectrum of a contaminant solution with a contaminant concentration of 40 mg/L is shown at 156, the spectrum of a contaminant solution with a contaminant concentration of 20 mg/L is shown at 158, the spectrum of a contaminant solution with a contaminant concentration of 4 mg/L is shown at 160, the spectrum of a contaminant solution with a contaminant concentration of 2 mg/L is shown at 162, the spectrum of a contaminant solution with a contaminant concentration of 0.4 mg/L is shown at 164, and the spectrum of a contaminant solution with a contaminant concentration of 0.2 mg/L is shown at 166. The spectrum of D4 cyclomethicone with no contaminant is shown at 168. With the y-direction resolution of graph 150 shown, the spectra of contaminant solutions with a contaminant concentration less than or equal to 2 mg/L are not resolved. However, as shown in FIG. 7, described below, spectral differences between contaminant solutions with a contamination concentration of less than 2 mg/L are sufficient to provide a limit of quantitation of about 0.75 mg/L (0.75 ppm) tetradecane in water.

Vibrational spectroscopy measurements, such as FTIR, can also be performed on contaminant solutions in siloxane solvents in other IR absorbance regions, such as those ranging in wave number between 3200 $cm^{-1}$ and 2700 $cm^{-1}$ and between 1800 $cm^{-1}$ and 1300 $cm^{-1}$. Absorbance bands centered at wave numbers of 1460 $cm^{-1}$ and 1377 $cm^{-1}$ are shown in FIG. 1. The hydrocarbon IR absorbance regions just described have low overlap with the absorbance regions of the siloxane solvents.

Current and previously-published vibrational spectroscopy methods from ASTM, EPA and ISO for oil-in-water also specify that a clean-up filtration operation be performed to remove any grease. Grease has a strong absorption peak in a band ranging in wave number between 1780 $cm^{-1}$ and 1700 $cm^{-1}$. Siloxane solvents are devoid of significant absorption peaks in this range of wave numbers so that the concentration of grease in a siloxane solvent can be measured directly by vibrational spectroscopy, such as FTIR, with minimal overlap with the absorption spectrum of the siloxane solvent.

As will be described in greater detail below, the measurement processes described herein are calibrated using a set of calibration solutions composed of different defined quantities of a hydrocarbon dissolved in a defined quantity of a siloxane solvent. In an example, the hydrocarbon is tetradecane and the siloxane solvent is D4 cyclomethicone. The resulting set of calibration solutions is similar to that specified in ASTM D7678.

In embodiments of the method that use D4 cyclomethicone as the siloxane solvent may be calibrated using a set of calibration solutions in which a hydrocarbon other than tetradecane is dissolved in D4 cyclomethicone. Embodiments of the method that use a siloxane solvent other than D4 cyclomethicone are calibrated using a set of calibration solutions having different defined quantities of tetradecane or another hydrocarbon dissolved in a defined quantity of the siloxane solvent used by the embodiment of the methods. In an example, the methods are calibrated using a set of calibration solutions composed of different defined quantities of K010 oil dissolved in a defined quantity of the siloxane solvent used by the method, e.g., D4 cyclomethicone. K010 oil is a mixture of 50% diesel oil and 50% lubricating oil sold by the Bundesanstalt für Materialforschung und-prüfung (BAM), Berlin, Germany. K010 oil is the calibration material specified by the ISO 9377-2 GC-FID method.

The vibrational spectra of the calibration solutions are measured using a vibrational spectrometer. In an example, the vibrational spectrometer is an FTIR spectrometer such as Agilent® 5500t FTIR spectrometer or a Cary 630 DialPath FTIR spectrometer, both sold by Agilent Technologies, Inc., Santa Clara, Calif. These spectrometers are capable of generating spectra similar to those shown in FIG. 2.

Calibrations that relate the measured IR spectra of the calibration solutions to the known concentration of the hydrocarbon in the calibration solutions are generated. The relationship between measured IR absorbance and concentration is described by what is commonly called Beer's law or the Beer-Lambert law. The Beer-Lambert law states that absorbance of an analyte in a sample is proportional to the concentration of the analyte in the sample, which is also dependent on the path length (thickness) and absorptivity (constant) of the analyte at a given wave number or in a given wave number range. The Beer-Lambert law is commonly used in spectroscopy to relate measured absorbance values to respective concentration values obtained from the spectra of a set of known calibration standards. Modern computing allows mathematical modeling of Beer's Law absorbance to concentration correlations at multiple wave numbers or or in multiple wave number ranges of the IR spectrum.

In an example, a chemometric partial least squares (PLS) analysis is performed using Solo chemometric software and Model Exporter software licensed by Eigenvector Research, Inc. Wenatchee, Wash. The PLS calibrations generated by the Eigenvector software are inserted into MicroLab PC software licensed by Agilent Technologies, Inc. When the spectrometer is later used to measure the vibrational spectrum of a contaminant solution under test, the MicroLab PC software additionally receives from the spectrometer a set of spectral data representing the vibrational spectrum of the contaminant solution. The MicroLab PC software uses the calibrations to convert the spectral data to a concentration of a hydrocarbon contaminant in the contaminant solution and, hence, in the sample from which the hydrocarbon contaminant was extracted by the siloxane solvent. After calibration, the measurement method can be used by a non-technical user in accordance with simple instructions to step the user through the sampling procedure.

FIG. 3 is a screenshot 180 showing how the MicroLab PC software displays a result for TPH derived from each spectral measurement performed by the vibrational spectrometer. The result shown in FIG. 3 is generated based on the assumption that the sample preparation and extraction procedures specified in ASTM-D7678 have been performed. Failure to subject the contaminant solution to a clean-up filtration operation prior to measurement can result in an erroneously high TPH result if the original sample includes grease. Measuring the hydrocarbon concentration of the contaminant solution before the contaminant solution is subject to a clean-up filtration operation generates a total oil and grease (TOG) measurement. After the TOG measurement, the clean-up filtration operation is performed. In an example, 1 gram of anhydrous sodium sulfate is added to the contaminant solution as a water removal agent and 1 gram of dried Florisil® ($MgO_3Si$) is added a grease removal agent. The contaminant solution is then filtered, and a second measurement of the hydrocarbon concentration of the contaminant solution is performed. The second measurement produces a total petroleum hydrocarbons (TPH) measurement.

FIG. 3 shows a TPH result of 9.71 mg/L for a validation sample with the prepared concentration of 10 mg/L of K010 oil. The measurement process generates results that meet the ASTM-D7678 validation specifications for precision (7.3% at 12.5-13.9 mg/$L^2$), bias (900±12 mg/L of oil in the extraction solvent), and percent recovery (70-130%).

FIG. 4 is a flowchart showing an example 200 of a method for performing solvent extraction to quantify contamination of a sample by a hydrocarbon contaminant. In block 210, a defined quantity of the sample is provided. In block 220, a defined quantity of a siloxane solvent is provided. In block 230, the defined quantity of the sample and the defined quantity of the siloxane solvent are mixed to form a contaminant solution that includes the hydrocarbon contaminant dissolved in the siloxane solvent. In block 240, the contaminant solution is separated from the sample.

FIG. 5 is a flowchart showing an example 300 of a method for determining the concentration of a hydrocarbon contaminant in a sample. Elements of method 300 that correspond to elements of method 200 are indicated using the same reference numeral. In block 210, a defined quantity of the sample is provided. In block 220, a defined quantity of a siloxane solvent is provided. In block 230, the defined quantity of the sample and the defined quantity of the siloxane solvent are mixed to extract the hydrocarbon contaminant from the sample to form a contaminant solution with the siloxane solvent. In block 240, the contaminant solution is separated from the sample. In block 350, the concentration of the contaminant in the separated contaminant solution is measured by vibrational spectroscopy.

In block 210, in an example, the defined quantity of the sample is provided by measuring out a defined volume or weight of the sample. In another example, a container containing a defined quantity of the sample is received at the location where the solvent extraction or the determination of the concentration of the hydrocarbon contaminant is to be carried out.

In block 220, in an example, the defined quantity of the siloxane solvent is provided by measuring out a defined weight or volume of the siloxane solvent. In another example, to save having to measure out the siloxane solvent, pre-packaged containers each containing a defined quantity of the siloxane solvent are purchased, and the contents of one or more of the pre-packaged containers are used to provide the measured quantity of a siloxane solvent.

In block 230, in an example, the defined quantity of the sample and the defined quantity of the siloxane solvent are mixed by shaking by hand. In other examples, mixing is accomplished mechanically using a mechanical shaker, a homogenizer, a sonicator, a blender, or another suitable mechanism, by stirring by hand or mechanically, or by using another suitable mixing technique. Mixing the sample with the siloxane solvent contacts the hydrocarbon contaminant that constitutes part of the sample with the siloxane solvent. The siloxane solvent extracts the hydrocarbon contaminant from the sample to form the contaminant solution in which the hydrocarbon contaminant is dissolved in the siloxane solvent.

In block 240, in an example, since the siloxane solvent is immiscible with the sample, and differs in density from the sample, the mixture of the contaminant solution and the sample are allowed to separate into layers. The contaminant solution is the predominant component of one of the layers that will be referred to as a contaminant solution layer. The sample is predominant in another of the layers that will be referred to as a solution layer. In some examples, separation into layers is promoted by centrifugation.

FIG. 4 additionally shows in block 250 an operation that may be performed on the contaminant solution obtained using method 200. In block 250, the contaminant solution is analyzed. In an example, contaminant solution layer is analyzed in situ, i.e., while the contaminant solution layer is still in contact with the sample layer. In another example, a portion of the contaminant solution layer is removed for analysis. The analysis of the removed portion of the contaminant solution layer may be performed at the same location as the preparation of the contaminant solution. Alternatively, the removed portion of the contaminant solution layer may be dispatched to a remote location for analysis.

In an example, the contaminant solution is analyzed by vibrational spectroscopy to determine the concentration of the hydrocarbon contaminant therein. Examples of vibrational spectroscopy include infrared spectroscopy, Fourier transform infrared spectroscopy (FTIR), near-infrared spectroscopy, far-infrared spectroscopy, infrared laser spectroscopy, and Raman spectroscopy. In some embodiments, Raman spectroscopy or near-infrared spectroscopy is used to analyze the contaminant solution layer in situ.

In other examples, the contaminant solution is analyzed by other types of spectroscopy such as ultraviolet spectroscopy, visible light spectroscopy and fluorescence spectroscopy. In other examples, the contaminant solution is analyzed by gravimetric analysis, gas or liquid chromatography, or nuclear magnetic resonance (NMR). Instruments and methods of using such instruments to perform the above-mentioned analyses are known and may be used.

Referring now to FIG. 5, in block 350, the concentration of the contaminant in the separated contaminant solution is measured by vibrational spectroscopy. In an example, a portion of the contaminant solution layer is removed to measure the concentration of the hydrocarbon contaminant in the separated contaminant solution. In another example, the concentration of the hydrocarbon contaminant in the separated contaminant solution is measured in situ, as described above. The concentration of the hydrocarbon contaminant in the separated contaminant solution may be made at the same location as the contaminant solution is prepared, or elsewhere, as described above. Examples of vibrational spectroscopy are described above.

In an example of the use of method 200 to extract a contaminant from a sample prior to measuring the concentration of an oil contaminant in water, or the use of method 300 to measure the concentration of an oil contaminant in water, in preparation for performing the method, all glassware that will contact the sample was thoroughly cleaned, rinsed with distilled water and dried at 130° C. Then, prior to performing the method, the glassware was rinsed with clean (pure) D4 cyclomethicone solvent and dried. In an example, the method was performed using a 1 L sample bottle with a fluoropolymer liner or a wide-necked glass flask with a ground neck with either a glass or fluoropolymer stopper. A sample of process water sample was collected directly, per ASTM Practice D3370, using the 1 L sample bottle and the siloxane solvent was added to the sample in the same sample bottle. Samples not subject to solvent extraction within 1-2 days of collection were acidified with hydrochloric acid to prevent microbial growth in the sample, in accordance with ASTM D7678. Validation samples using this method with and without acidification were found to have very satisfactory results, and within the ASTM D3921 and D7678 specifications for precision and bias.

In block 210, a 900 mL water sample of process water or waste water was measured out. In an example, a 900 mL water sample was measured out into the above-mentioned 1L glass bottle. In another example, a pre-measured 900 mL water sample is received for analysis. In block 220, 20 mL of D4 cyclomethicone were measured out. In an example, a clean plastic (HDPE) disposable syringe, a volumetric pipette, or a reusable glass syringe was rinsed with clean D4 cyclomethicone and was then used to measure out 20 mL of D4 cyclomethicone. The plastic syringe should be devoid of black rubber components. In another example, a 20 mL vial of D4 cyclomethicone is provided.

In block 230, the D4 cyclomethicone was added to the water sample and the resulting mixture was vigorously shaken for one to two minutes. In block 240, the mixture was allowed to separate into a contaminant solution layer on top of a sample layer. In an example, the contaminant solution layer was allowed to separate from the sample layer for one to two hours, or until a defined contaminant solution layer had become visible. Optionally, magnesium sulfate ($MgSO_4$) was added to the mixture to break up emulsions and/or improve layer separation.

In block 250 of method 200 and in block 350 of method 300, pure deionized, reverse osmosis filtered, or reagent water was added to the bottle until the bottle was filled into the neck area to facilitate removal of at least part of the contaminant solution layer. A disposable pipette was then used to remove a portion of the contaminant solution layer. In block 250 of method 200, the removed portion of the contaminant solution layer was analyzed. In block 350 of method 300, the concentration of the hydrocarbon contaminant in the removed portion of the contaminant solution layer was measured using vibrational spectroscopy. In an example, a small amount, approximately 0.25 mL, of the removed contaminant solution layer was transferred to an FTIR spectrometer for spectral analysis. In some configurations, the contaminant solution was transferred to the measurement cell of the infrared spectrometer and the infrared spectrometer measured the spectrum of the contaminant solution by transmitting infrared light through a defined path length of the contaminant solution in the measurement cell (transmissive mode). In other configurations, the contaminant solution was transferred to a reflective measurement surface of the infrared spectrometer, and the infrared spectrometer measured the spectrum of the contaminant solution by reflecting infrared light off the measurement surface with which the contaminant solution was in contact (reflective mode). In an example, the removed portion of the contaminant solution layer was transferred to a DialPath or TumblIR measurement cell that was integrated into a 5500/4500 series FTIR spectrometer or a Cary 630 FTIR spectrometer for spectral analysis. In an example, the FTIR spectrometer was used to measure the concentration of an oil contaminant in the contaminant solution and, hence, in the sample.

In another example, in block 240, a 2000 mL separatory funnel was cleaned and then rinsed with D4 cyclomethicone. Another suitable phase separation container that would allow a contaminant solution layer to form may be used instead of the separatory funnel. About three-quarters of the mixture formed in block 230 was added to the separatory funnel. The remainder one-quarter of the mixture was then vigorously shaken and then quickly transferred to the separatory funnel. The contents of the separatory funnel were then left to allow a contaminant solution layer to form. In block 250 of method 200, the contaminant solution in the contaminant solution layer was analyzed as described above. In block 350 of method 300, the concentration of the contaminant in the contaminant solution in the contaminant solution layer was measured, also as described above.

In some embodiments, in block 250 of method 200, the contaminant solution is measured by subjecting the contaminant solution layer, once it has separated from the sample layer, to Raman spectroscopy while the contaminant solution layer is still in contact with a sample layer. In some embodiments, in block 350 of method 300, the concentration of a hydrocarbon contaminant in the contaminant solution is measured by subjecting the contaminant solution layer, once it has separated from the sample layer, to Raman spectroscopy while the contaminant solution layer is still in contact with the sample layer. Performing Raman spectroscopy while the contaminant solution is still in contact the sample layer obviates the need to remove at least a portion of the contaminant solution layer from the sample layer before analysis or measurement.

To calibrate the above-described measurement methods, a set of calibration samples was prepared. Each calibration sample had a different concentration of an exemplary hydrocarbon (tetradecane) in the siloxane solvent provided in block 220 of methods 200 and 300. In an example, nine calibration samples with the concentrations of tetradecane in D4 cyclomethicone shown in Table 2 were prepared in accordance with ASTM D7678. The concentrations of tetradecane in the set of calibration samples ranged from zero to 18,341 mg/L of tetradecane in D4 cyclomethicone. This range of tetradecane concentrations in D4 cyclomethicone corresponds to a range of concentrations ranging from zero to 407.6 mg/L of oil in water after extraction and applying the enrichment factor of 45 specified in ASTM D7678 in which 20 mL of solvent are used to extract a hydrocarbon contaminant from 900 mL of water.

TABLE 2

Calibration Set
Tetradecane (TD) in D4 Cyclomethicone

| Calibration Solution | mg/L in D4 | equivalent mg/L in water |
|---|---|---|
| Solution Blank | 0.0 | 0.0 |
| Solution A | 9.2 | 0.2 |
| Solution B | 18.3 | 0.4 |
| Solution C | 91.7 | 2.0 |
| Solution D | 183.4 | 4.1 |
| Solution E | 917.1 | 20.4 |
| Solution F | 1834.1 | 40.8 |
| Solution G | 9170.5 | 203.8 |
| Solution S | 18341.0 | 407.6 |

The vibrational spectrum of each calibration sample was then measured. In an example, the infrared spectrum of each calibration sample was measured three times using two different models of FTIR spectrometer, an Agilent 5500t and a Cary 630. Similar to the methodology prescribed in ASTM D3921-96 and ASTM D7678, the measured FTIR spectra were subjected to a partial least squares (PLS) regression analysis over the wave number range from 2890 to 2790 cm$^{-1}$. Three PLS calibrations were generated using the above-mentioned Solo chemometric software and Model Exporter software to cover the entire concentration range with no more than 3 latent variables (factors). The PLS calibrations generated by the Eigenvector software were inserted into the above-mentioned MicroLab PC software where they were used to convert spectral data representing the measured vibrational spectrum of a contaminant solution under test to a concentration of the hydrocarbon contaminant in the contaminant solution and, hence, by applying the appropriate enrichment factor, to a concentration of a hydrocarbon contaminant in a sample of water.

Figure 6:
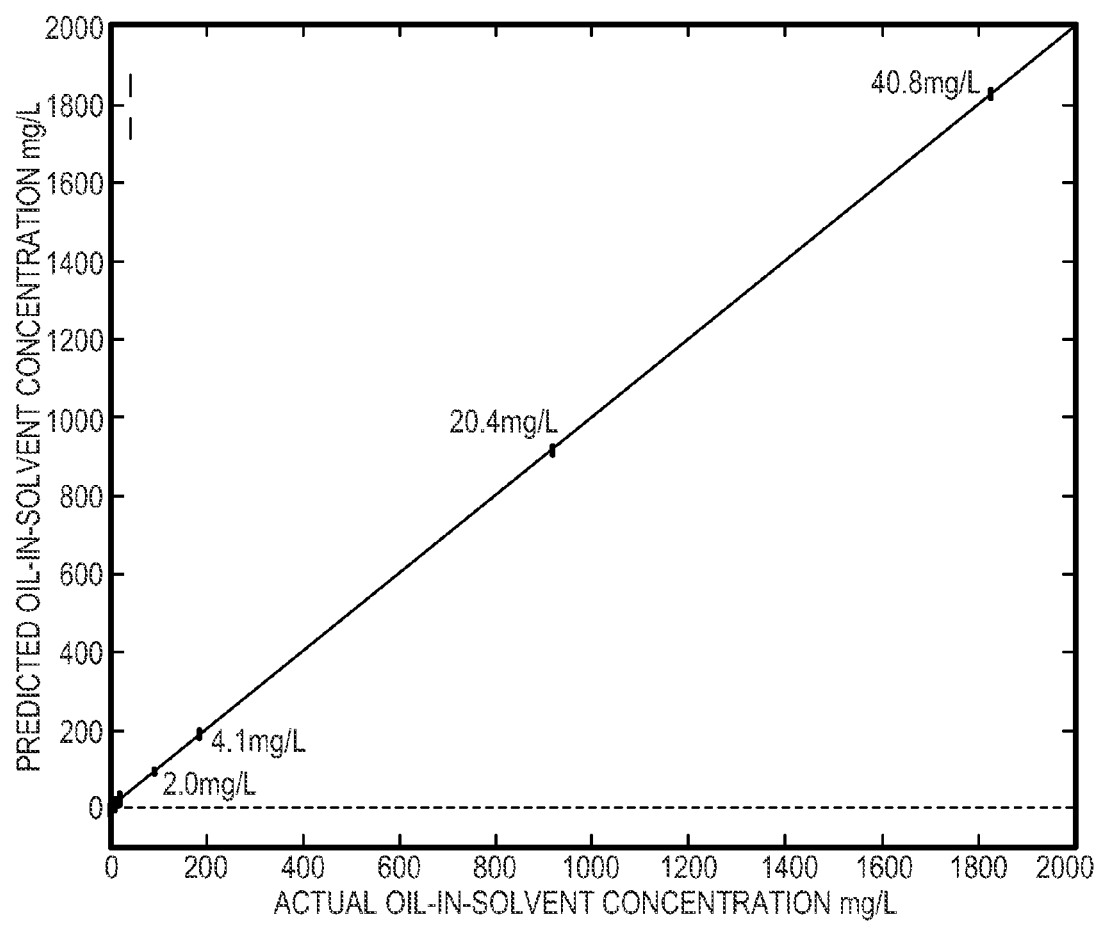
FIG. 6 is a predicted-versus-actual graph showing the results of the mid-range calibration performed as described above using calibration samples of tetradecane in D4 cyclomethicone.

FIG. 6 is a predicted-versus-actual graph showing the results of the mid-range calibration performed as described above using calibration samples of tetradecane in D4 cyclomethicone. FIG. 7 is a predicted-versus-actual graph showing the results of the low-range calibration performed as described above using calibration samples of tetradecane in D4 cyclomethicone. The predicted values are those generated by the MicroLab PC software from the measured vibrational spectra of the calibration samples using the calibrations obtained as described above. The actual values are the known concentrations of tetradecane in the calibration solutions. In FIGS. 6 and 7, the labels on the curve are final oil in water values, i.e., the enrichment factor of 45 has been applied, whereas the concentrations displayed along the axes of the graphs are concentrations of tetradecane in D4 cyclomethicone in the calibration solutions. The calibrations show close agreement between predicted and actual, with correlation coefficients of $R^2=0.994938$ (low range), $R^2=0.999895$ (mid-range), and $R^2=0.996866$ (high range).

To verify the calibration, the vibrational spectrum of Solution E (917.1 mg/L tetradecane in D4 cyclomethicone) of the calibration set was measured using an FTIR spectrometer and the measured vibrational spectrum was converted to a tetradecane concentration using the MicroLab PC software calibrated as described above. The vibrational spectrum of calibration solution E was measured three times to generate respective sets of spectral data. The MicroLab PC software was then used to calculate a respective tetradecane concentration from each set of spectral data. Table 3 shows the result of each measurement, and the difference between each measurement and the known concentration of tetradecane in calibration sample E. The maximum difference allowed by ASTM D7678-11 between the measured concentration and the known concentration is ±12 mg/L tetradecane in D4 cyclomethicone. All the differences are well below this limit, so the calibration is verified in accordance with ASTM D7678-11.

TABLE 3

Calibration Verification
using Solution E (917.1 mg/L tetradecane in D4 cyclomethicone)

| Sample | Measured Tetradecane in D4 mg/L | Difference from actual mg/L | max allowed difference mg/L |
|---|---|---|---|
| Rep 1 | 923.06 | 6.01 | ±12 |
| Rep 2 | 913.36 | −3.69 | ±12 |
| Rep 3 | 909.52 | −7.53 | ±12 |
| Mean Value | 915.31 | | |
| Std. Deviation | 6.98 | | |
| Rel. Std. Dev. % | 0.76 | | |

Five oil-in-water validation standards were created to test the precision, accuracy, and percent recovery of methods 200 and 300. Each of the validation standards had a concentration of 10 mg/L K010 oil in water. Each of the validation standards was subject to the full solvent extraction process, including the above-described acidification to preserve the sample, and the above-described clean-up filtration. The first four samples were used to demonstrate compliance with the Initial Laboratory Capability specifications set forth in ASTM D7678-11. Results are shown in Table 4. The Initial Laboratory Capability specification requires that the measurements of four 10 mg/L K010 oil-in-water replicate samples have an accuracy within a range from 8.74 to 10.14 mg/L and have a precision characterized by a relative standard deviation of 7.3% or better. The measurements of all the samples are within the accuracy range and the relative standard deviation is 3.55%, which is less than half the limit. Accordingly, methods 200 and 300 pass the single laboratory validation requirements of ASTM D7678-11 and demonstrate the initial laboratory capability. The average percentage recovery for the samples is 94.4%, which is well within the ASTM recovery range from 70% to 130%.

TABLE 4

Laboratory Capability Verification
10 mg/L K010 oil in water, full process

| Sample | measured K010 oil in water mg/L |
|---|---|
| Prep 1 | 8.96 |
| Prep 2 | 9.48 |
| Prep 3 | 9.71 |
| Prep 4 | 9.62 |
| Mean Value | 9.44 |
| Std. Deviation | 0.34 |
| Rel. Std. Dev. % | 3.55 |
| Recovery % | 94.4 |

The fifth validation standard had a concentration of 10.3 mg/L K010 oil in water and was subject to the full solvent extraction process, as described above. The vibrational spectra of seven aliquots of the contaminant solution layer obtained in block 240 of methods 200 and 300 were measured using FTIR spectrometers, and the MicroLab PC software was used to calculate a respective concentration of K010 oil in water from the vibrational spectrum measured for each aliquot. Results are shown in Table 5. The relative standard deviation is 3.23% (precision) and a percent recovery of 92.51%. This sample also passed the ASTM 7678-11 accuracy and precision requirements. The similar single laboratory test detailed in ASTM 7678-11 on the seven aliquots of the contaminant solution layer yielded a similar relative standard deviation of 3.59% (10 mg/L K010 oil).

TABLE 5

Precision Validation
10.3 mg/L K010 oil in water, full process

| | measured K010 oil in water mg/L |
|---|---|
| Prep 5 Rep 1 | 9.26 |
| Prep 5 Rep 2 | 9.31 |
| Prep 5 Rep 3 | 9.22 |
| Prep 5 Rep 4 | 10.09 |
| Prep 5 Rep 5 | 9.72 |
| Prep 5 Rep 6 | 9.56 |
| Prep 5 Rep 7 | 9.54 |
| Mean Value | 9.53 |
| Std. Deviation | 0.31 |
| Rel. Std. Dev. % | 3.23 |
| Recovery % | 92.51 |

A siloxane solvent can be used to extract a hydrocarbon contaminant from a sample of a particulate matrix, such as sand or soil, by substituting the siloxane solvent for the solvent specified in EPA 418.1, ASTM D3921-96, DIN 38409 H18, or another standard extraction method. EPA 418.1 has been commonly used for measuring oil contamination in solid matrices "industrial and domestic wastes", but is no longer in use due to its requirement for banned Freon® 113 (1,1,2-Trichloro-Trifluoroethane) extraction solvent. The DIN 38409 H18 method also specifies the use of Freon® 113 as the extraction solvent and has been used historically in European laboratories for the measurement of hydrocarbon contaminants in particulate matrix materials such as soils. The procedure specified in these methods is essentially the same as that for oil in water extractions.

In a method based on the above-mentioned methods, in which a siloxane solvent is used to extract a hydrocarbon contaminant from a sample of a particulate matrix material, a defined quantity of a sample of contaminated particulate matrix material is provided by weighing out a defined weight of the sample and transferring the weighed-out quantity of the sample to a container. A defined quantity of a siloxane solvent sufficient to extract the contaminant from the weighed-out quantity on the sample is added to the container and the defined quantity of the sample and the defined quantity of the siloxane solvent are mixed. Mixing the sample and the siloxane solvent extracts the hydrocarbon contaminant from the sample to form a contaminant solution with a siloxane solvent. The contaminant solution is then separated from the sample. In an example, a Soxhlet extractor is used to aid in the separation of the siloxane solvent from the sample. The infrared spectrum of an aliquot of the contaminant solution is then measured by vibrational spectroscopy or another suitable method. The spectral measurement determines the absorption of infrared light by the hydrocarbon contaminant dissolved in the contaminant solution. The spectral measurement is converted to a concentration of the hydrocarbon contaminant in the siloxane solvent and, hence, in the sample, by calibrating the spectrometer or other measurement instrument using a calibration procedure similar to that described above. After the contaminant solution has been separated from the sample, and prior to the spectral measurement, the contaminant solution may be subject to a clean-up operation to remove grease, water, and suspended particulate matter from the contaminant solution.

Figure 8:
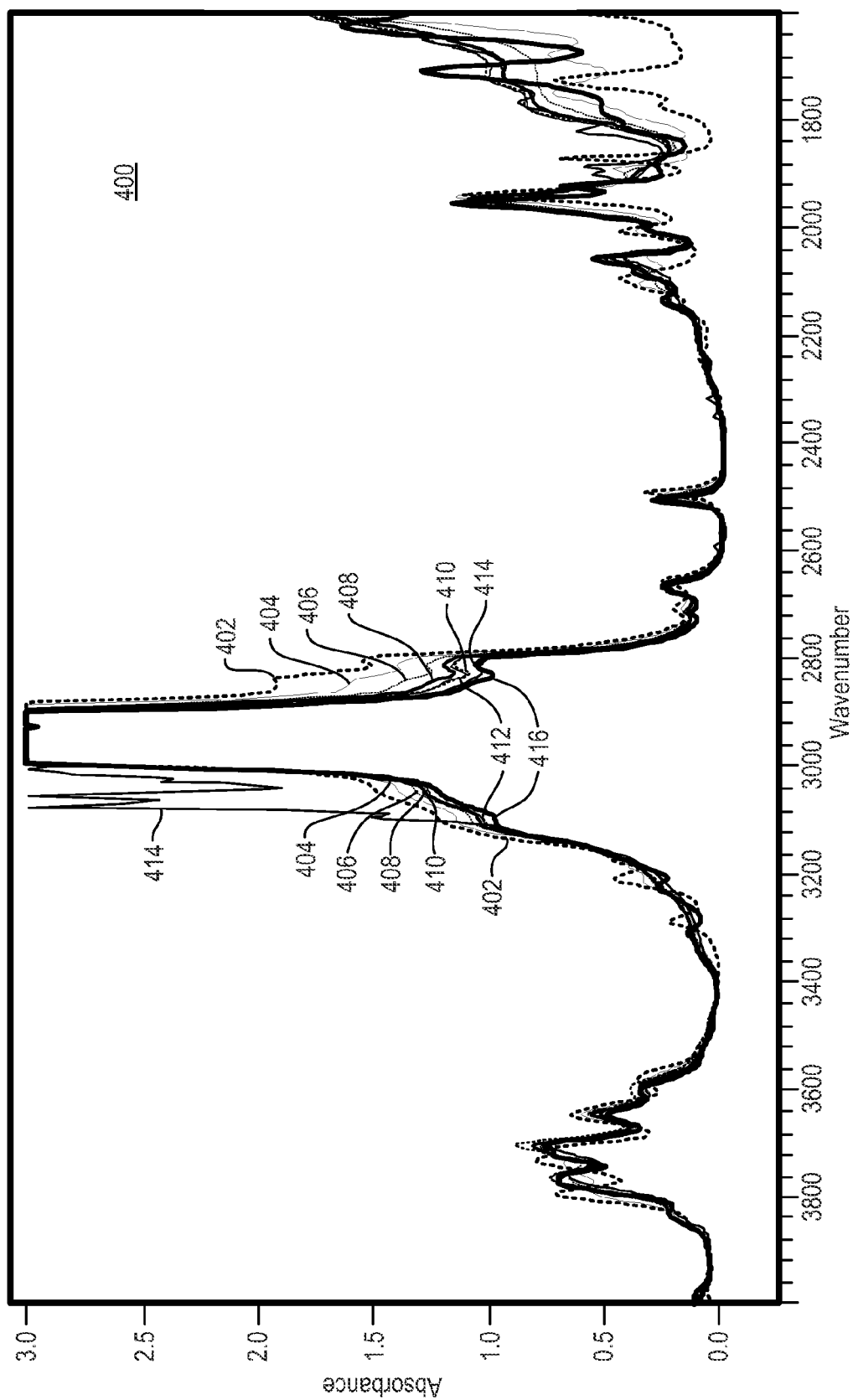
FIG. 8 is a graph showing a portion of the infrared spectra between wave numbers $3800\ cm^{-1}$ and $1800\ cm^{-1}$ of exemplary siloxane solvents.

Siloxane solvents other than D4 cyclomethicone can be used to extract hydrocarbon contaminants from samples of water or of a particulate matrix, such as soil, with subsequent quantitative analysis by vibrational spectroscopy or another suitable measurement technique. FIG. 8 is a graph showing a portion of the infrared spectra between wave numbers 3800 cm$^{-1}$ and 1800 cm$^{-1}$ of the exemplary siloxane solvents set forth above in Table 1. Specifically, FIG. 8 shows the infrared spectra between wave numbers 3800 cm$^{-1}$ and 1800 cm$^{-1}$ of the following siloxane solvents: hexamethyldisiloxane (0.65 cst) at 402, decamethyltetrasiloxane (1.5 cst) at 404, polydimethysiloxane (5 cst) at 406, polydimethylsiloxane (20 cst) at 408, polydimethylsiloxane (100 cst) at 410, polydimethylsiloxane (500 cst) at 412, phenylmethylsiloxane Dow Corning 510® Fluid (50 cst) at 414, and D4 cyclomethicone at 416. Hexamethyldisiloxane, decamethyltetrasiloxane, polydimethysiloxane (5 cst), polydimethylsiloxane (20 cst), polydimethylsiloxane (100 cst), polydimethylsiloxane (500 cst) are examples of linear siloxane solvents, whereas D4 cyclomethicone is an example of a cyclic siloxane solvent. Cyclic siloxane solvents range in size based on the number of siloxy (Si—O) bonds in the cyclic ring. For example, D5 cyclomethicone has five Si—O groups or unique Si—O—Si bonds in the ring. Other examples of cyclic siloxane solvents are more complex structures that form cages or cubic cage structures with various Si—O bonds. Siloxane solvents can be created from the reaction of silanols which are often the oxidation products of the cyclic siloxanes. Phenylmethylsiloxane Dow Corning 510® Fluid (50 cst) contains some amount of a phenyl substituted siloxane polymer, which can be created using phenylmethyl silanols as a starting "monomer" to polymerize. Siloxane solvents can also be substituted with Si—H (hydrogen substituted) or amines groups (amino silanes or amino siloxanes). Various other functional siloxane solvents are manufactured for specific desired properties, such as crosslinking additives and functionalized coatings for weatherproofing applications.

The infrared spectra of all of the exemplary siloxane solvents include regions that are available for the use of vibrational spectroscopy to measure the concentration of aromatic or aliphatic hydrocarbons dissolved in the siloxane solvent. A siloxane solvent that has absorbance, at a given IR wavelength and path length, of less than 5 can be considered to be not totally absorbing and therefore capable of allowing measurement of the concentration of a dissolved hydrocarbon contaminant that absorbs at the given wavelength. FIG. 8 indicates that all the tested siloxane solvents have an absorbance of less than 2 in the wave number range from 2890 $cm^{-1}$ to 2700 $cm^{-1}$ where aliphatic hydrocarbons such as mineral oils or diesel fuel oils absorb, and all but phenylmethyl siloxane has an absorbance of less than 2 in the wave number range from 3200 to 3000 $cm^{-1}$ of aromatic/olefinic hydrocarbons. The absorbances of the siloxane solvents were measured in transmission mode with a 500 μm path length.

The oil-in-water extraction performance of four of the siloxane solvents shown in FIG. 8 was tested. Water samples were prepared by adding 27 mg K010 oil (see above) to 900 mL of water to produce a water sample with 30 mg/L of a hydrocarbon contaminant. The sample was thoroughly mixed before adding 20 mL of the siloxane solvent under test. The resulting mixture was vigorously mixed and allowed to settle until the contaminant solution layer separated to the top of the container. At least part of the contaminant solution layer was then removed and 1 gram of anhydrous sodium sulfate was added to remove any water from the contaminant solution. The contaminant solution was then filtered to remove particles, and the filtered contaminant solution was added to a standard 500 μm path length DialPath measurement cell. The IR spectrum of the contaminant solution in the measurement cell was measured over a wave number range from 2890 $cm^{-1}$ to 2790 $cm^{-1}$ using an FTIR spectrometer as described above. Each of the siloxane solvents was tested using the process just described. Additionally, the vibrational spectrum of each siloxane solvent with no hydrocarbon contaminant was measured on the same wave number range using an FTIR spectrometer.

Figure 9:
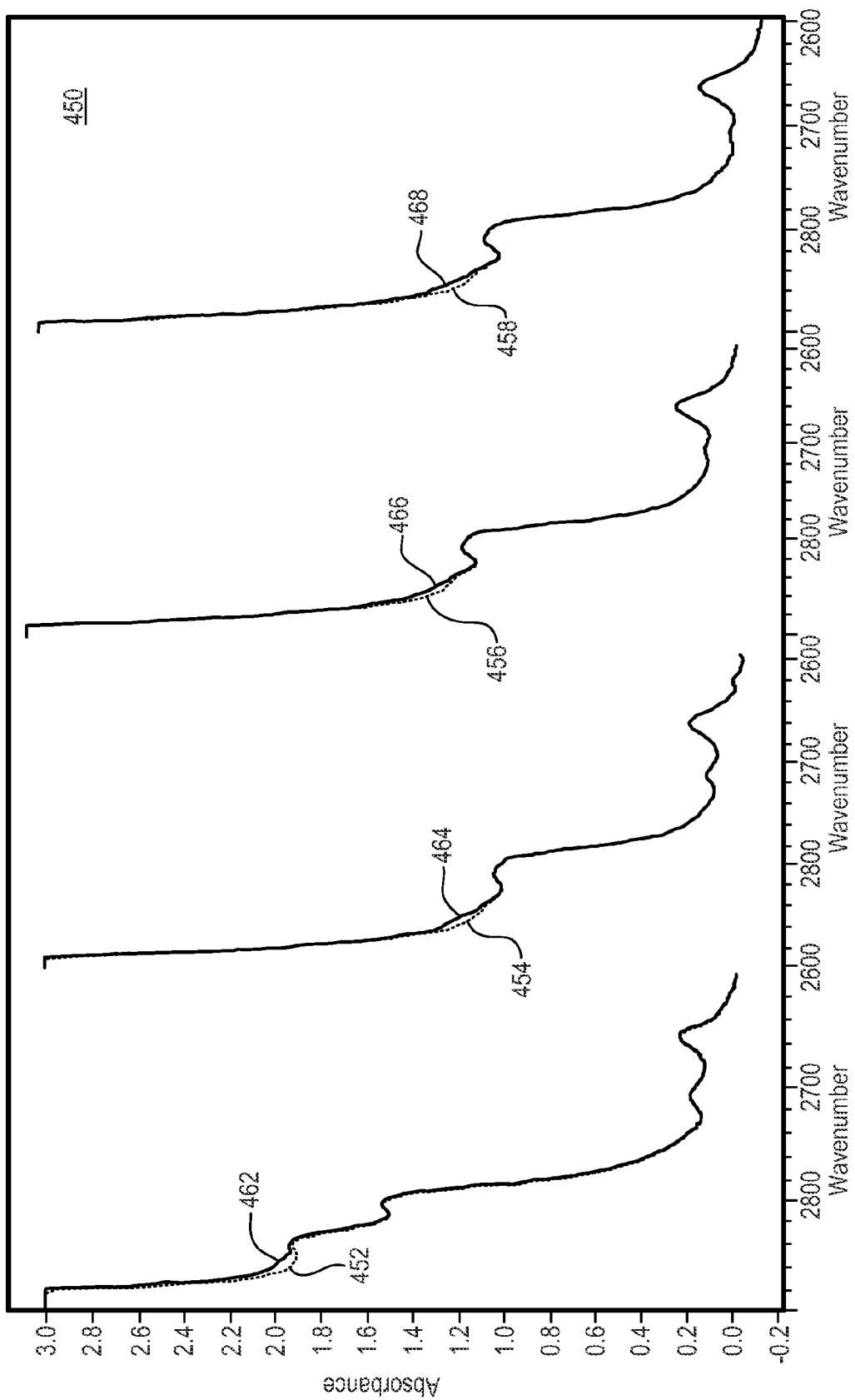
FIG. 9 is a set of graphs showing portions of the measured infrared spectra of four different siloxane solvents before and after performing solvent extraction on a sample of hydrocarbon-contaminated water.

FIG. 9 is a set of graphs 450 showing portions of the measured infrared spectra of the four siloxane solvents before and after performing solvent extraction on the above-described water sample. Specifically, FIG. 9 shows portions of the measured infrared spectrum of hexamethyldisiloxane (0.65 cst) before at 452 and after at 462, phenylmethylsiloxane (50 cst) before at 454 and after at 464, polydimethylsiloxane (100 cst) before at 456 and after at 466, and polydimethylsiloxane (500 cst) before at 458 and after at 468. Polydimethylenesiloxane is a polymer: the two examples tested differ in their viscosities due to their having different numbers of the dimethylenesiloxane monomer.

In the wave number range from 2890 $cm^{-1}$ to 2790 $cm^{-1}$ shown in FIG. 9 for hydrocarbon in-phase $CH_2$ (2858 $cm^{-1}$) and $CH_3$ (2878 $cm^{-1}$) stretch indicates that the siloxane solvents tested extracted similar amounts of the hydrocarbon contaminant from the water. The difference in absorption indicated by the difference between the before and after infrared spectra for each siloxane solvent tested represents the concentration of the hydrocarbon contaminant. The difference between the before and after spectra can be measured and a calibration technique similar to that described above for D4 cyclomethicone can be used to convert the difference between the before and after spectra to a concentration of the hydrocarbon contaminant.

The above-described results indicate that methods 200 and 300 described above with reference to FIGS. 4 and 5 have analytical performance equal to or better than ASTM D7678-11, while being much easier to use. Methods 200 and 300 use siloxane solvents that are CFC free, VOC exempt, odorless, colorless, low to moderately flammable, non-toxic, and safe for incidental skin contact. Some are even used in cosmetic products. This removes many concerns regarding the environmental impact of conventional harmful extraction solvents and sample handling of conventional highly flammable solvents, such as cyclohexane. Methods 200 and 300 allow for a mobile and easy-to-use oil-in-water oil-in-particulate-matrices measurement, with comparable results to lab-based FTIR and GC-FID systems. Methods 200 and 300 are calculated to be 21 times less cost per sample compared to most other FTIR ASTM OIW methods, including the Freon®-based ASTM D3921 and fluorinated trimer (S-316) solvent-based ASTM D7066-04. Results from validation standards indicate as good or better performance than the published ASTM D7678 validation results.

This disclosure describes the invention in detail using illustrative embodiments. However, the invention defined by the appended claims is not limited to the precise embodiments described.

We claim:

1. A method for performing solvent extraction to quantify contamination of a sample by a hydrocarbon contaminant, the method comprising:
   providing a defined quantity of the sample;
   providing a defined quantity of a siloxane solvent;
   mixing the defined quantity of the sample and the defined quantity of the siloxane solvent to extract the hydrocarbon contaminant from the sample to form a contaminant solution with the siloxane solvent;
   separating the contaminant solution from the sample; and
   subjecting at least a portion of the separated contaminant solution to one of: molecular spectroscopic analysis; or gravimetric analysis; or nuclear magnetic resonance (NMR) spectroscopic analysis.

2. The method of claim 1, in which the siloxane solvent comprises octamethylcyclotetrasiloxane.

3. The method of claim 1, in which the siloxane solvent comprises hexamethyldisiloxane 0.65 cst, dimethyl, phenylmethylsiloxane, trimethyl-terminated 50 cst, polydimethylsiloxane 100 cst, or polydimethylsiloxane 500 cst.

4. The method of claim 1, in which the siloxane solvent comprises polydimethylsiloxane, dimethicone, cyclomethicone, decamethyltetrasiloxane, hexamethyldisiloxane, or a functionalized siloxane liquid.

5. The method of claim 1, in which the siloxane solvent has a viscosity in a range from 0.3 to 500 cSt.

6. The method of claim 1, additionally comprising dispatching at least a portion of the separated contaminant solution to a remote location for analysis.

7. The method of claim 1, including subjecting at least a portion of the separated contaminant solution to molecular spectroscopic analysis.

8. The method of claim 7, in which the molecular spectroscopic analysis is infrared spectroscopic analysis.

9. The method of claim 1, including subjecting at least a portion of the separated contaminant solution to nuclear magnetic resonance (NMR) spectroscopic analysis.

10. The method of claim 1, including subjecting at least a portion of the separated contaminant solution to gravimetric analysis.

11. A method of determining a concentration of a hydrocarbon contaminant in a sample, the method comprising:
providing a defined quantity of the sample;
providing a defined quantity of a siloxane solvent;
mixing the defined quantity of the sample and the defined quantity of the siloxane solvent to extract the hydrocarbon contaminant from the sample to form a contaminant solution with the siloxane solvent;
separating the contaminant solution from the sample; and
measuring the concentration of the hydrocarbon contaminant in the separated contaminant solution using vibrational spectroscopy.

12. The method of claim 11, in which the siloxane solvent comprises octamethylcyclotetrasiloxane.

13. The method of claim 11, in which the siloxane solvent comprises hexamethyldisiloxane 0.65 cSt, dimethyl, phenylmethylsiloxane, trimethyl-terminated 50 cSt, polydimethylsiloxane 100 cSt, or polydimethylsiloxane 500 cSt.

14. The method of claim 11, in which the siloxane solvent comprises polydimethylsiloxane, dimethicone, cyclomethicone, decamethyltetrasiloxane, hexamethyldisiloxane, or a functionalized siloxane liquid.

15. The method of claim 11, in which the siloxane solvent has a viscosity in a range from 0.3 to 500 cSt.

16. The method of claim 11, in which the measuring comprises measuring the concentration using infrared light having a wavelength corresponding to a vibrational resonance of an aliphatic or aromatic group.

17. The method of claim 11, in which the measuring comprises measuring the hydrocarbon concentration using a vibrational spectrum in a wave number region from 3200 $cm^{-1}$ to 2700 $cm^{-1}$.

18. The method of claim 11, in which the measuring comprises measuring the hydrocarbon concentration using a vibrational spectrum in a wave number region from 1800 $cm^{-1}$ to 1300 $cm^{-1}$.

19. The method of claim 11, in which the sample consists essentially of water.

20. The method of claim 19, in which the siloxane solvent comprises octamethylcyclotetrasiloxane.

21. The method of claim 11, in which the sample consists essentially of a particulate matrix.

22. The method of claim 21, in which the sample consists essentially of soil.

* * * * *